US008647320B2

(12) United States Patent
Proksch et al.

(10) Patent No.: US 8,647,320 B2
(45) Date of Patent: Feb. 11, 2014

(54) DEVICE FOR INTRODUCING MEDICINE INTO AN INFUSION CONTAINER

(75) Inventors: Karl-Heinz Proksch, Felsberg (DE); Julian Titze, Leeds (DE); Helmut Freigang, Körle (DE)

(73) Assignee: B. Braun Melsungen AG, Melsungen (DE)

( * ) Notice: Subject to any disclaimer, the term of this patent is extended or adjusted under 35 U.S.C. 154(b) by 167 days.

(21) Appl. No.: 12/680,734

(22) PCT Filed: Sep. 30, 2008

(86) PCT No.: PCT/EP2008/008283

§ 371 (c)(1), (2), (4) Date: Jun. 21, 2010

(87) PCT Pub. No.: WO2009/046903

PCT Pub. Date: Apr. 16, 2009

(65) Prior Publication Data

US 2011/0004184 A1 Jan. 6, 2011

(30) Foreign Application Priority Data

Oct. 1, 2007 (DE) ........................ 10 2007 046 951

(51) Int. Cl.
*A61B 19/00* (2006.01)

(52) U.S. Cl.
USPC .......................................................... 604/407

(58) Field of Classification Search
USPC .......................................................... 604/407
See application file for complete search history.

(56) References Cited

U.S. PATENT DOCUMENTS

| | | | | | |
|---|---|---|---|---|---|
| 2,816,550 | A | * | 12/1957 | Hudson | 604/413 |
| 2,973,758 | A | * | 3/1961 | Murrish | 604/413 |
| 3,882,909 | A | * | 5/1975 | Ogle | 141/286 |
| 3,885,607 | A | * | 5/1975 | Peltier | 141/329 |
| 3,938,518 | A | * | 2/1976 | Tischlinger | 604/413 |
| 3,941,171 | A | * | 3/1976 | Ogle | 141/309 |
| 3,945,382 | A | * | 3/1976 | Ogle | 604/413 |
| 3,987,791 | A | * | 10/1976 | Chittenden et al. | 604/413 |
| RE29,656 | E | * | 6/1978 | Chittenden et al. | 604/413 |
| 4,233,973 | A | * | 11/1980 | Shukla | 604/84 |
| 4,392,850 | A | * | 7/1983 | Elias et al. | 604/82 |
| 4,411,662 | A | * | 10/1983 | Pearson | 604/411 |
| 4,432,755 | A | * | 2/1984 | Pearson | 141/329 |
| 4,434,823 | A | * | 3/1984 | Hudspith | 141/329 |
| 4,607,671 | A | * | 8/1986 | Aalto et al. | 141/329 |
| 4,623,334 | A | * | 11/1986 | Riddell | 604/85 |
| 4,624,667 | A | * | 11/1986 | Rutnarak | 604/414 |
| 4,759,756 | A | * | 7/1988 | Forman et al. | 604/413 |
| 4,820,269 | A | * | 4/1989 | Riddell | 604/85 |
| 4,865,583 | A | * | 9/1989 | Tu | 604/508 |
| 4,886,495 | A | * | 12/1989 | Reynolds | 604/88 |
| 4,898,209 | A | * | 2/1990 | Zbed | 137/614.04 |
| 4,936,841 | A | * | 6/1990 | Aoki et al. | 604/413 |
| 5,049,129 | A | * | 9/1991 | Zdeb et al. | 604/85 |
| 5,304,163 | A | * | 4/1994 | Bonnici et al. | 604/403 |
| 5,308,347 | A | * | 5/1994 | Sunago et al. | 604/403 |
| 5,334,170 | A | * | 8/1994 | Moroski | 604/80 |
| 5,342,346 | A | * | 8/1994 | Honda et al. | 604/413 |
| 5,364,386 | A | * | 11/1994 | Fukuoka et al. | 604/411 |
| 5,397,303 | A | * | 3/1995 | Sancoff et al. | 604/82 |
| 5,423,753 | A | * | 6/1995 | Fowles et al. | 604/87 |
| 5,445,631 | A | * | 8/1995 | Uchida | 604/412 |
| 5,478,337 | A | * | 12/1995 | Okamoto et al. | 604/413 |
| 5,647,845 | A | | 7/1997 | Haber et al. | |
| 5,807,312 | A | * | 9/1998 | Dzwonkiewicz | 604/30 |
| 5,833,213 | A | * | 11/1998 | Ryan | 251/149.1 |
| 5,879,345 | A | * | 3/1999 | Aneas | 604/411 |
| 5,893,397 | A | * | 4/1999 | Peterson et al. | 141/27 |
| 5,989,237 | A | * | 11/1999 | Fowles et al. | 604/413 |
| 6,036,680 | A | * | 3/2000 | Horne et al. | 604/414 |
| 6,071,270 | A | * | 6/2000 | Fowles et al. | 604/413 |
| 6,086,560 | A | * | 7/2000 | Kriesel | 604/131 |
| 6,209,738 | B1 | * | 4/2001 | Jansen et al. | 215/247 |
| 6,270,481 | B1 | * | 8/2001 | Mason et al. | 604/181 |
| 6,277,095 | B1 | * | 8/2001 | Kriesel et al. | 604/132 |
| 6,390,120 | B1 | * | 5/2002 | Guala | 137/512.15 |
| 6,475,206 | B1 | * | 11/2002 | Hama et al. | 604/411 |
| 6,508,791 | B1 | * | 1/2003 | Guerrero | 604/183 |
| 6,537,263 | B1 | * | 3/2003 | Aneas | 604/412 |
| 6,558,365 | B2 | * | 5/2003 | Zinger et al. | 604/410 |
| 6,571,837 | B2 | * | 6/2003 | Jansen et al. | 141/329 |
| 6,575,955 | B2 | * | 6/2003 | Azzolini | 604/411 |
| 6,582,415 | B1 | * | 6/2003 | Fowles et al. | 604/413 |
| 6,719,728 | B2 | * | 4/2004 | Mason et al. | 604/181 |
| 6,723,076 | B1 | * | 4/2004 | Strobel | 604/262 |
| 7,077,835 | B2 | * | 7/2006 | Robinson et al. | 604/413 |
| 7,297,140 | B2 | * | 11/2007 | Orlu et al. | 604/411 |
| 7,404,814 | B2 | * | 7/2008 | Shiraishi et al. | 604/416 |
| 2002/0065490 | A1 | * | 5/2002 | Heinz et al. | 604/205 |
| 2002/0123736 | A1 | * | 9/2002 | Fowles et al. | 604/413 |
| 2003/0105448 | A1 | * | 6/2003 | Shiraishi et al. | 604/415 |
| 2003/0187420 | A1 | * | 10/2003 | Akerlund et al. | 604/408 |
| 2003/0191445 | A1 | * | 10/2003 | Wallen et al. | 604/411 |

(Continued)

FOREIGN PATENT DOCUMENTS

WO WO 03/079956 A1 10/2003

OTHER PUBLICATIONS

International Search Report from corresponding International Application No. PCT/EP2008/008283, filed Sep. 30, 2008 (3 pages).

(Continued)

*Primary Examiner* — Tatyana Zalukaeva
*Assistant Examiner* — Guy K Townsend
(74) *Attorney, Agent, or Firm* — Klein, O'Neill & Singh, LLP

(57) ABSTRACT

A device for adding a medicine to an infusion solution in an infusion container having a removal opening provided with a seal area. A transfer cap, which has a first hollow spike for piercing the seal area, is connected to the removal opening of the infusion container. A receiving means for a medicine container is formed at the transfer cap, which has a second hollow spike for piercing a seal at the medicine container. A valve is arranged between the first and second hollow spikes in the transfer cap, where the valve interrupts the connection between the first and second hollow spikes and can be moved into the open position by the action of a force.

20 Claims, 12 Drawing Sheets

(56) References Cited

U.S. PATENT DOCUMENTS

| | | | | |
|---|---|---|---|---|
| 2003/0199847 | A1 * | 10/2003 | Akerlund et al. | 604/411 |
| 2003/0229330 | A1 * | 12/2003 | Hickle | 604/411 |
| 2004/0073175 | A1 * | 4/2004 | Jacobson et al. | 604/251 |
| 2006/0186045 | A1 * | 8/2006 | Jensen et al. | 210/645 |
| 2007/0282278 | A1 * | 12/2007 | Knight | 604/236 |
| 2007/0282297 | A1 * | 12/2007 | Knight | 604/500 |
| 2011/0279271 | A1 * | 11/2011 | Monroe | 340/568.1 |

OTHER PUBLICATIONS

Written Opinion from corresponding International Application No. PCT/EP2008/008283, filed Sep. 30, 2008 (5 pages).

* cited by examiner

DEVICE FOR INTRODUCING MEDICINE INTO AN INFUSION CONTAINER

This is a U.S. national phase application under 35 U.S.C. §371 of International Patent Application No. PCT/EP2008/008283, filed Sep. 30, 2008, and claims the benefit of priority to German patent application DE 10 2007 046 951.0 filed Oct. 1, 2007, the contents of each of which are expressly incorporated herein by reference as if set forth in full.

BACKGROUND

1. Field

The present disclosure relates to a device for introducing a medicine into an infusion container, which is provided with a sealed removal opening.

2. Related Art

Before an infusion set with a drip chamber is attached to an infusion container for carrying out an intravenous infusion, it is known to add a medicine to the infusion solution. Generally, a medicine container, having a transfer cap with a hollow spike used for piercing a seal at the infusion container is attached to the removal opening of the infusion container, which also has a receiving means for the medicine container.

After connecting the infusion container to the medicine container, infusion solution is displaced into the medicine container by repeatedly compressing and releasing the flexible infusion container. After dissolving and adding medicine to the infusion solution, the arrangement is rotated such that the infusion container is situated below and the medicine container above, whereupon the contents of the medicine container are drawn by suction back into the infusion container by again repeatedly compressing and releasing the flexible infusion container. Next, the medicine container having the transfer cap is removed from the infusion container and the infusion set is attached to the infusion container, whereupon the infusion can begin.

This procedure is associated with the risk of contamination of the infusion solution because after removing the medicine container, the removal opening of the infusion container is exposed and contaminating ambient air can enter the infusion container.

SUMMARY

The present disclosure provides a device and associated method for adding medicine to the infusion solution in the infusion container while reducing the risk of contamination.

This object is solved according to the invention by the features of claim 1. However, the invention is not limited to the features of claim 1 for various aspects of the invention are disclosed throughout the specification and are depicted in the appended drawings. The medicine container is not released from the transfer cap after adding the medicine to the infusion solution, thus allowing the infusion to be carried out while the medicine container is at the infusion container. Thus, the system of the present disclosure for infusing medicine into the infusion solution is maintained in a closed state, thus reducing the risk of contamination of the infusion solution.

In one aspect, a device is provided for adding a medicine to an infusion solution in an infusion container having a removal opening provided with a seal area. The device includes a transfer cap connectable to the removal opening of the infusion container, where the transfer cap has a first hollow spike configured for piercing the seal area. A receiving means is provided for a medicine container formed on the transfer cap, where the receiving means has a second hollow spike configured for piercing a seal of the medicine container. The device also includes a valve arranged between the first and second hollow spikes in the transfer cap, where the valve interrupts the connection between the first and second hollow spikes and where the valve can be moved into an open position only by the action of a force.

In another aspect, a device is provided for adding a medicine to an infusion solution, which includes a hollow cylindrical member including a first hollow spike configured for piercing a seal area on a removable opening. The device also includes a tubular hub coupled to the hollow cylindrical member and configured to receive a container in a locking arrangement. The tubular hub includes a second hollow spike configured for piercing a seal of the container. A valve is positioned between the first and second hollow spikes, where the valve is manipulatable by the action of a force to open the valve and allow flow between the first hollow spike and the second hollow spike.

In yet another aspect, a method is provided for adding a medicine to an infusion solution in an infusion container having a removal opening provided with a seal area. The method comprises coupling a hollow cylindrical member including a first hollow spike and piercing the seal area on the removable opening; coupling a tubular hub including a second hollow spike to a medicine container in a locking arrangement, and piercing a seal of the medicine container; and actuating a valve positioned between the first and second hollow spikes to open the valve and allow a flow through the first hollow spike and the second hollow spike from between the infusion container and the medicine container.

An advantage of the present infusion set is simplified handling and increased safety since it is no longer necessary to remove the medicine container from the infusion container which allows the health care worker to read at any time which medicine has been added to the infusion solution by reference to the medicine container.

BRIEF DESCRIPTION OF THE DRAWINGS

Device, system, and method for introducing medicine into an infusion container are explained in more detail below with reference to the drawings, in which.

DETAILED DESCRIPTION

The detailed description set forth below in connection with the appended drawings is intended as a description of the presently preferred embodiments of a device for adding medicine to an infusion container or transfer device and is not intended to represent the only forms in which the present device, system, and method may be constructed or used. The description sets forth the features and the steps for constructing and using the transfer device of the present disclosed embodiments in connection with the illustrated figures and examples. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

Figure 1:
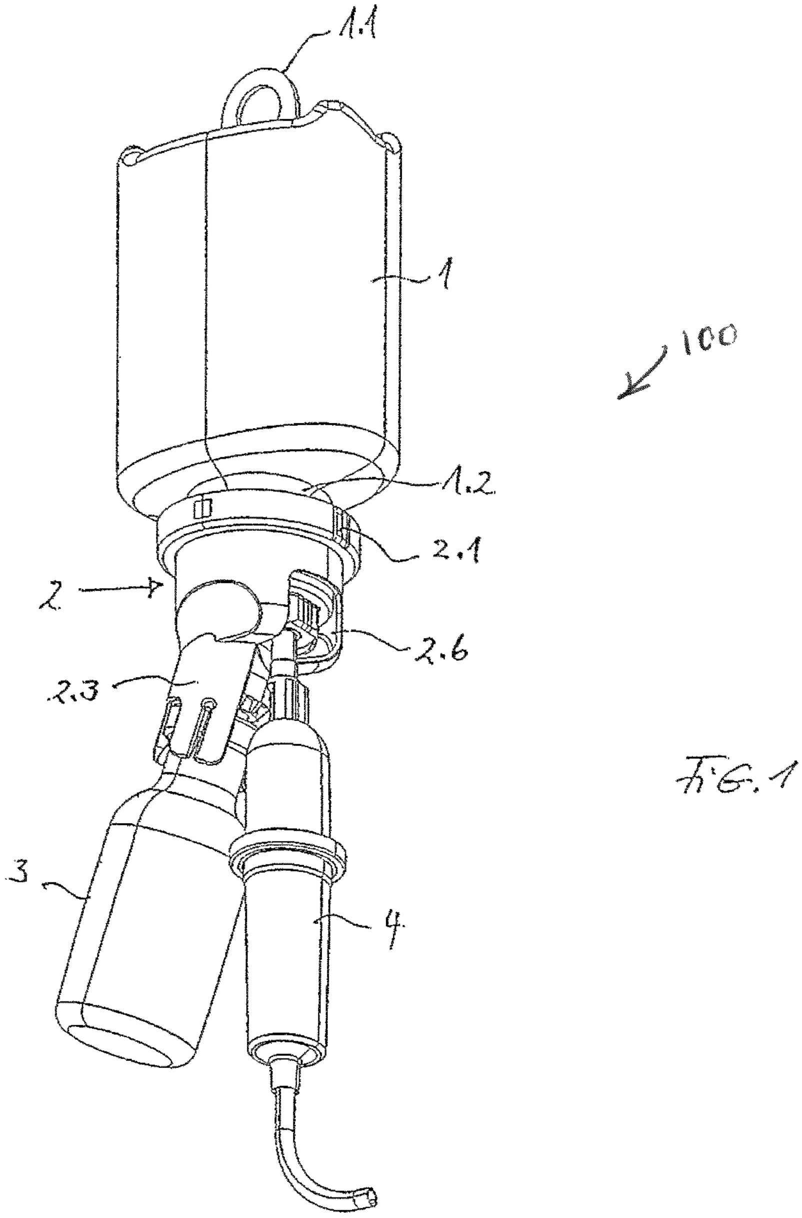
FIG. 1 shows a perspective view of an infusion container having a medicine container and a drip chamber coupled thereto in a ready state for carrying out an infusion.

FIG. 1 shows a perspective view of an infusion set 100 having, an infusion container 1 coupled to a medicine container 3 and a drip chamber 4 in a ready state for carrying out an infusion. FIG. 1 shows the bottle-shaped infusion container 1 as generally comprising a transparent synthetic material having flexible wall portions. The flexible wall portions of the infusion container 1 may be compressed and released for generating pressure in the infusion container 1, whereupon on release thereof, low pressure is generated due to the flexible wall portions returning to their original position. A loop 1.1 for suspending the infusion container 1 may be provided on the upper side of the infusion container 1. On the lower or opposing side, the infusion container 1 is provided with a bottleneck 1.2 to which a transfer cap 2 may be attached. The medicine container 3, usually made of glass or similar material, is inserted in the transfer cap 2 with its axis inclined to the axis of the infusion container 1. The drip chamber 4 of the infusion set may be connected to the infusion container 1.

FIG. 1 shows an embodiment of the operating position of the infusion set in which an infusion may be carried out, where the drip chamber 4 is arranged with its axis essentially parallel or vertical (not inclined) to the axis of the infusion container 1. In other embodiments, the drip chamber 4 is inclined or is parallel but offset.

Figure 2:
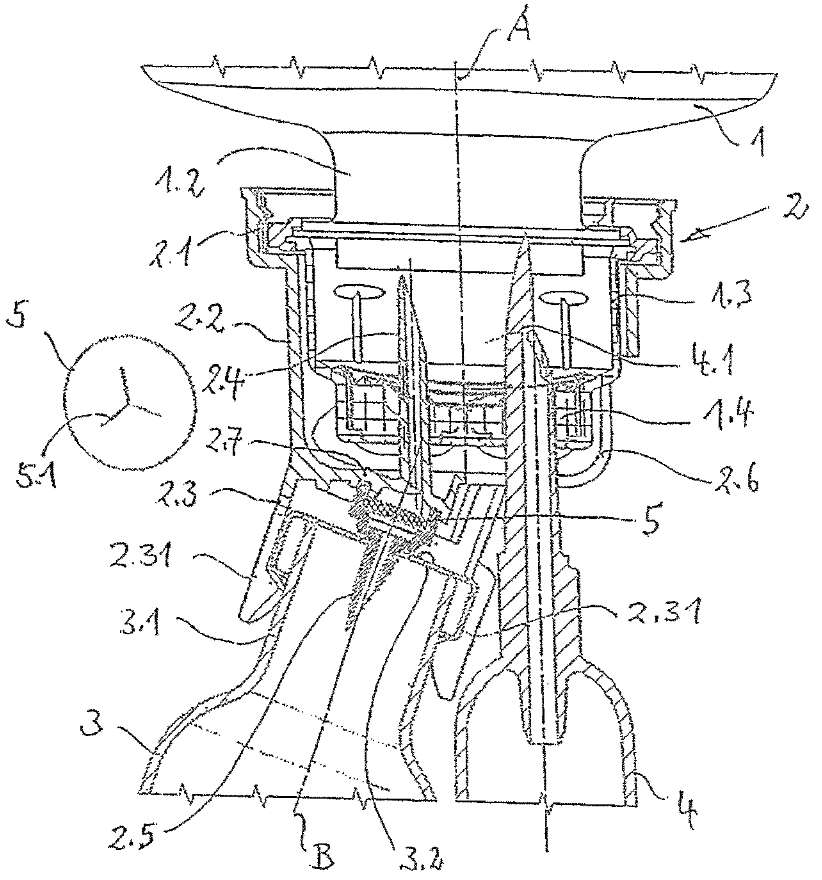
FIG. 2 shows a cross sectional view through the device having a transfer cap according to an embodiment.

FIG. 2 shows a cross sectional view of an embodiment of the transfer cap 2 in the operating position shown in FIG. 1. As shown in FIG. 2, a sealing cap 1.3 having a piercable seal area 1.4 is attached to the bottleneck 1.2 of the infusion container 1 in a liquid-impermeable manner, such as in a liquid tight seal. The transfer cap 2 with the bottleneck 1.2 having the seal cap 1.3 may be fixed at a flange portion (FIG. 1) by means of resilient locking portions 2.1, which releasably overlap the edge of the seal cap 1.3. Attached to the flange portion is a hollow cylindrical portion 2.2 of the transfer cap 2. As shown in FIG. 2, a tubular hub 2.3 is formed eccentrically such that the axis B thereof lies inclined to the axis A of the bottleneck 1.2 of the infusion container 1. The tubular hub 2.3 forms a receiving means for receiving a bottleneck 3.1 of the medicine container 3. The medicine container bottleneck 3.1 is provided with a flange or an enlarged cap section 2.50, which engages resilient hooks or detents 2.31 provided on the circumference of the tubular hub 2.3. The engagement between the flange 2.50 and the detents 2.31 locks the medicine container 3 in the connected position to the infusion container 1. Thus, an aspect of the present transfer device is a transfer cap comprising a first receiving end for receiving an infusion container and a second receiving end for receiving a medicine container, and wherein the first receiving end and the second receiving end engage the infusion container and the medicine container such that an axis of the medicine container is inclined relative to an axis of the infusion container. In another example, the infusion cap holds the infusion container and the medicine container such that a base end of the infusion container and a base end of the medicine container both face outwardly away from the first and second receiving ends.

In the area of the tubular hub 2.3, the transfer cap 2 is provided with a first hollow spike 2.4 on a side facing the infusion container 1. The first hollow spike 2.4 pierces the seal area 1.4 of the seal cap 1.3 when the transfer cap 2 is attached to the bottleneck 1.2 of the infusion container 1. A second hollow spike 2.5 is arranged at the transfer cap 2 such that it pierces a seal 3.2 of the medicine container 3 when the medicine container 3 is inserted into the tubular hub 2.3.

Thus, the transfer cap 2 allows the user to couple the hollow cylindrical portion 2.2 to the bottleneck 2.1 of the infusion container 1 while allowing the tubular hub 2.3 to be connected to a different container, such as the medicine container 3. The tubular hub 2.3 is arranged at an angle or inclined to the axis of the hollow cylindrical portion or member 2.2. The two parts may be locked together to form a single transfer cap 2 or may be made, either by moulding or casting, as a solid unitary member. The first hollow spike 2.4 is arranged substantially parallel to the axis of the hollow cylindrical portion 2.2 such that the piercing end of the first hollow spike 2.4 points to a seal area of the infusion container 1 when being coupled thereto. The second hollow spike 2.5 is arranged substantially parallel to the axis of the tubular hub 2.3 such that the piercing end of the second hollow spike 2.5 points to a seal on the medicine container 3 when being coupled thereto. In one embodiment, since the hollow cylindrical member 2.2 and the tubular hub 2.3 are arranged inclined to one another, the first and second hollow spikes are also arranged inclined to one another.

Between the first hollow spike 2.4 and the second hollow spike 2.5 in the transfer cap 2 is a valve 5 positioned to interrupt or block the connection between the first and second hollow spikes 2.4 and 2.5. In one embodiment, the valve opens to unblock the connection between the two hollow spikes only under the action of an actuating force. The actuating force may include the pressure created when compressing the infusion container either by manual manipulation or by using an automated process. Thus, actuating the valve positioned between the first and second hollow spikes causes the valve to open and allow a flow of liquid, such as a medication, through the first hollow spike 2.4 and the second hollow spike 2.5 from between the infusion container 1 and the medicine container 3.

In the embodiment shown in FIG. 2, the valve is formed as a resilient valve disc 5, which has three radial slits 5.1 in its middle area. The valve disc 5 is clamped on the circumference between two opposing sets of annular shoulders. The first set of annular shoulders is formed at a partition wall 2.7 of the transfer cap 2 upon which the first hollow spike 2.4 is moulded. The second opposing set of annular shoulders is formed at the flange of a member provided with the second hollow spike 2.5, which in this embodiment is inserted as a separate component part into the transfer cap 2 or in the area of the partition wall 2.7. It should be understood that the valve disc 5 may be clamped or held between the first and second hollow spikes 2.4 and 2.5 in any suitable manner that allows for the valve to operate or interrupt or block the flow of fluid through the first and second hollow spikes 2.4 and 2.5 and between the infusion container 1 and the medicine container 3. In another example, the valve is spring loaded and opens when an external force is applied but automatically closes when the external force drops below a certain minimum threshold, i.e., below the spring force.

Laterally, adjacent the eccentric inclined tubular hub 2.3, the transfer cap 2 is provided with a recess 2.6 (FIG. 1) through which the seal area 1.4 of the seal cap 1.3 is exposed to allow the infusion set having a hollow spike 4.1 at the drip chamber 4 to be inserted vertically by piercing the hollow spike 4.1 into the seal area 1.4 through the recess 2.6.

In the operating position shown in FIG. 2, infusion solution from the infusion container 1 can flow through the hollow spike 4.1 into the drip chamber 4 while the valve disc 5 maintains the connection between infusion container 1 and medicine container 3 in a closed state.

Figure 2A:
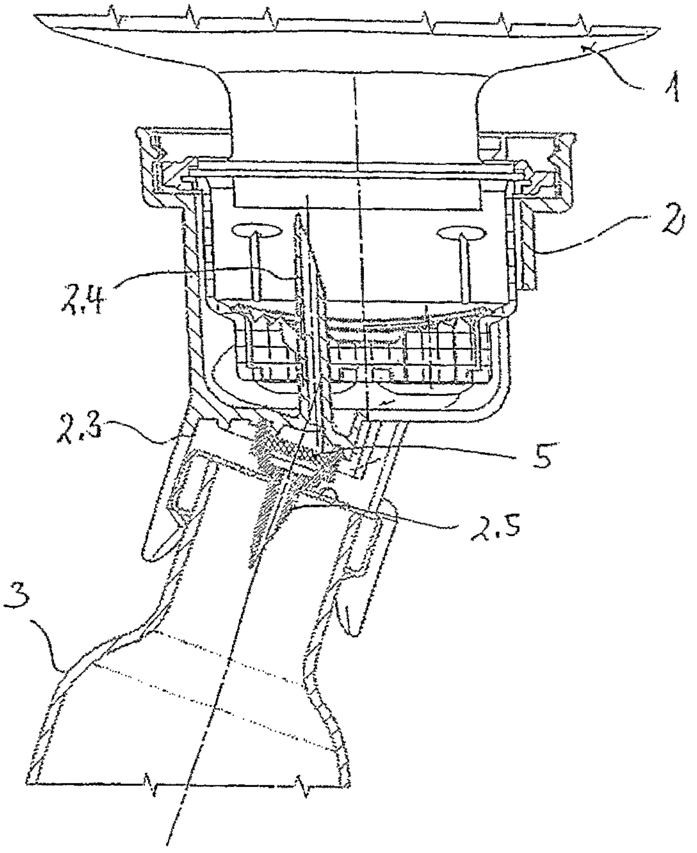
FIG. 2*a* shows the arrangement in FIG. 2 rotated by 180° in accordance with an embodiment.

In one embodiment, to add medicine to the infusion solution, the transfer cap 2 having the tubular hub 2.3 is first attached to the neck 3.1 of the medicine container 3, causing the second hollow spike 2.5 to pierce the seal 3.2 of the medicine container. In this embodiment, the transfer cap 2 is connected to the medicine container 3 in such a manner that the medicine container 3 cannot be detached from the transfer cap 2 without a tool. Once connected, as shown in FIG. 2*a*, the transfer cap 2 with the medicine container 3 is attached to the sealed infusion container 1, causing the first hollow spike 2.4 to pierce the seal area 1.4 of the infusion container. In one embodiment, the infusion container 1 can be positioned with the bottleneck located upwards and its base downwards so that the transfer cap 2 and the medicine container 3 are attached to the infusion container 1 from above. The closed valve 5 prevents leakage from the medicine container 3 so that its outlet can face the ground without spilling during the mounting process.

After installing the transfer cap 2 with the medicine container 3 to the infusion container 1 in the manner described above, the assembly is rotated 180° to correspond to the position shown in FIG. 2*a*. By repeatedly compressing the flexible walls of the infusion container 1, infusion solution is displaced into the medicine container 3. Due to the pressure exerted on the infusion container 1, the valve disc 5 opens by means of the valve lips located between the slits 5.1. The valve lips bend to allow the passage of infusion fluid into the medicine container 3. Thus, an exemplary method discussed herein is understood to include adding an infusion solution into a medicine container by piercing a first seal, piercing a second seal, and squeezing a container wall of an infusion container to force liquid into the medicine container. In a further example, a valve disc is forced to flap or swing open by pressure generated in squeezing the container wall, which allows fluid communication between the infusion container and the medicine container. In yet another example, the infusion container and the medicine container are first rotated before the squeezing step.

Figure 2B:
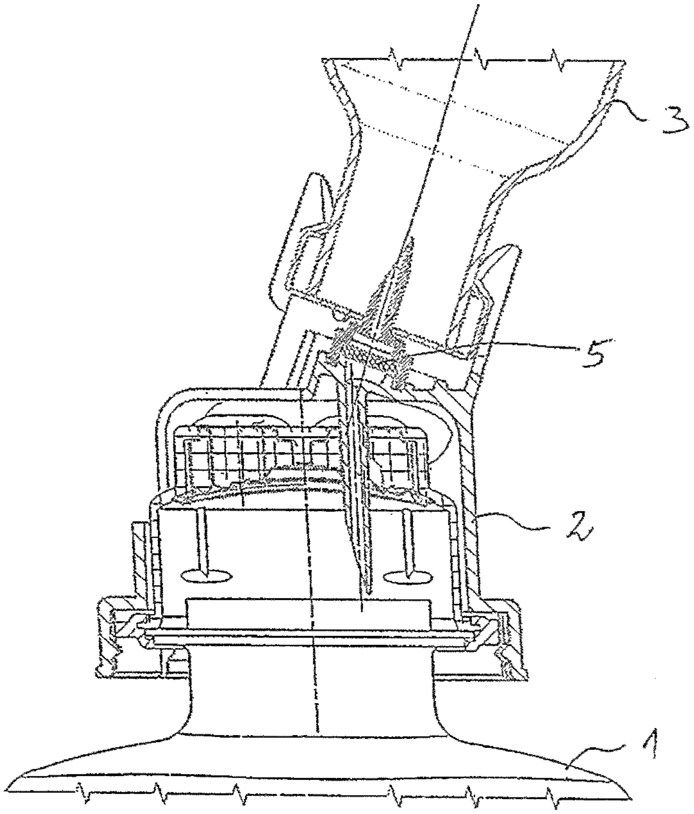
FIG. 2*b* shows the arrangement in FIG. 2 rotated vertically by 180° in accordance with an embodiment.

After dissolving and mixing the medicine and the infusion fluid in the medicine container 3, the arrangement is rotated vertically by 180° into the position shown in FIG. 2*b*. Again, by repeated compression of the infusion container 1, the medicine added to the infusion solution is drawn by suction from the medicine container 3 into the infusion container 1. In this case, the valve disc 5 opens due to the low pressure generated in the infusion container 1 after release of the compressed side walls of the infusion container 1. Thus, another embodiment disclosed herein is understood to include a method for mixing fluids in which a second rotation step is performed follow by further squeezing of the infusion container wall. On a broader level, examples discussed herein include passing fluid back and forth between two different containers prior to infusing a patient. In the specific examples discussed, the passing of fluid comprises piercing two different container seals with two different spikes that are in fluid communication with one another. To regulate the passing of fluid, a valve is provided between the two spikes. In one example, the valve may be actuated by pressure or by creating a differential pressure situation to force fluid to flow from a relatively higher pressure region to a relatively lower pressure region.

After the contents of the medicine container 3 have been transferred into the infusion container 1, which includes the original undiluted medicine contents as well as some of the infusion fluids, the hollow spike 4.1 of the drip chamber 4 is inserted by piercing into the seal area 1.4 of the infusion container 1 through the recess 2.6 in the transfer cap 2, whereupon the infusion can begin in the position shown in FIG. 1. In this position, the connection between the medicine container 3 and the infusion container 1 is interrupted by the valve disc 5, because no force is acting on the valve disc 5. Thus, no infusion fluid can flow back into the medicine container 3 located below the valve disc 5. The medicine container 3 is not releasably connected to the transfer cap 2 and remains in the position at the transfer cap 2 shown in FIGS. 1 and 2 while the infusion is being carried out. In one example, the entire contents of the medicine container 3 are drained into the infusion container before the drip chamber 4 is connected to the transfer cap 2. In another example, less than the entire contents of the medicine container 3 are drained before the drip chamber 4 is connected. Thus, a further feature of the present device, system, and method for transferring fluid includes transferring fluid from a first container into a second container, transferring fluid from the second container back to the first container, and then transferring fluid from the first container through a drip chamber for infusing a patient.

Since the medicine container 3 remains connected to the infusion container 1 during an infusion procedure, the medicine added to the infusion solution is immediately recognizable to operating personnel. Moreover, since the medicine container 3 is not released from the infusion container 1 or the transfer cap 2 after the mixing process, no contamination can occur in the connecting area between the medicine container 3 and the infusion container 1. After attaching the medicine container 3 to the infusion container 1, the system is maintained in a closed state. Thus, on a broader level, a feature of the present device, system, and method is a provision for blending medicine with infusion fluid using a transfer cap and wherein the cap retains the medicine container for at least part of the infusion process, and more preferably for the entire infusion process, for purposes of identifying contents of the infusion fluid and/or the medicine used for the infusion procedure.

The valve disc 5 makes it unnecessary to remove the medicine container 3 arranged in the transfer cap 2 between the first and second hollow spikes 2.4 and 2.5, which are arranged inclined to each other and separate from each other, allowing the valve disc 5 to be embodied in various ways.

Figure 3:
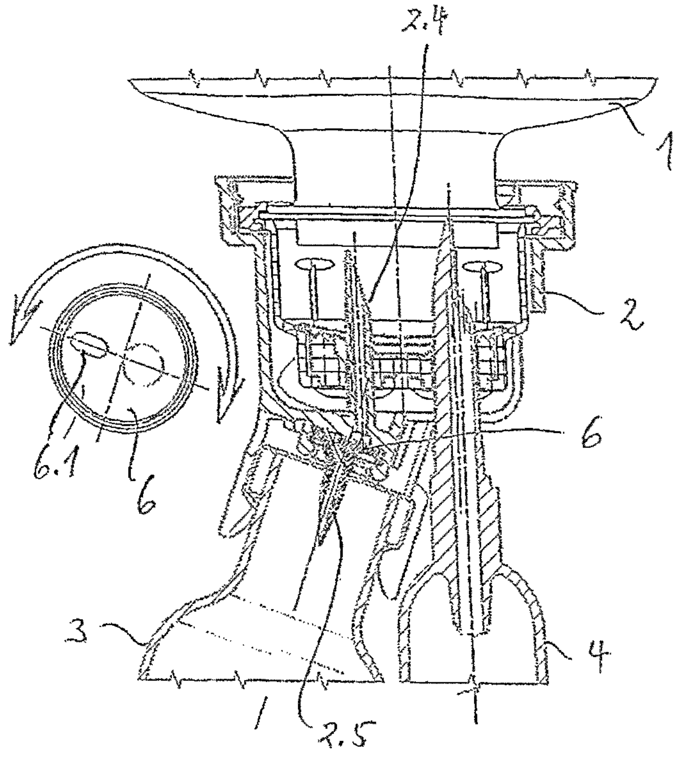
FIGS. 3 and 3*a* show a cross sectional view through the device having a valve disc which may be actuated by rotation in accordance with an embodiment.
Figure 3A:
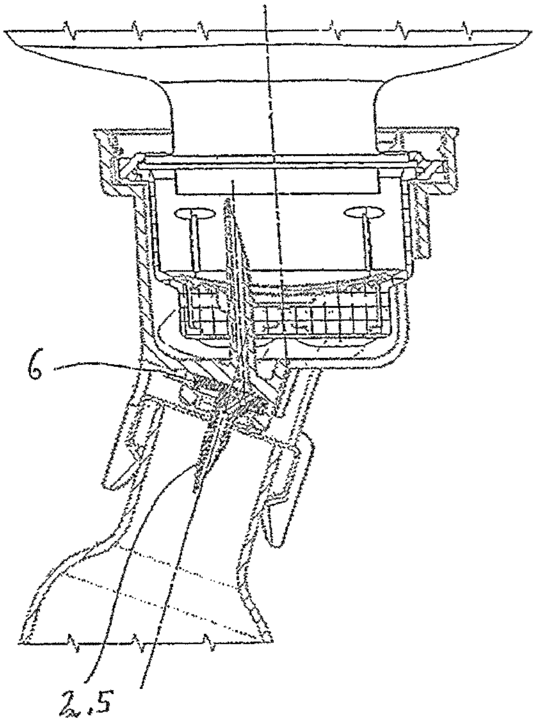

FIG. 3 shows a cross sectional view through the device having a valve disc which may be actuated by rotation in accordance with an embodiment. In this embodiment, a valve disc 6 is moulded at the second hollow spike 2.5, and is held twistably or rotatably between detents at the partition wall 2.7 of the transfer cap 2. The valve disc 6 is provided eccentrically with a through-channel 6.1, which can be aligned with the mouth opening of the first hollow spike 2.4. FIG. 3 shows the closed position of the valve disc 6, in which a closed area of the valve disc 6 is located opposite the mouth opening of the first hollow spike 2.4. FIG. 3*a* shows the connected position of the valve disc 6, in which the through-channel 6.1 is aligned with the first hollow spike 2.4.

To allow the valve disc 6 with the second hollow spike 2.5 moulded thereon to be twisted or rotated, a form fit is expediently formed between the seal 3.2 and the second hollow spike 2.5 by the second hollow spike 2.5 having, for example, an oval cross section. In this embodiment, by twisting the medicine container 3 in the tubular hub 2.3, the valve disc 6 can also be twisted into the open or closed position. Thus, when using the present embodiment, another rotational step is included, which is the rotational step of the valve. This rotational step is in addition to rotation the containers discussed above.

Figure 4:
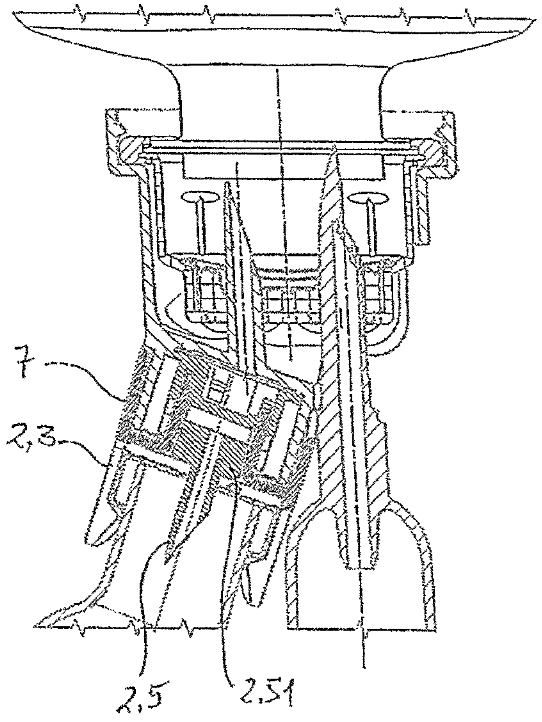
FIGS. 4 and 4*a* show a cross sectional view through the device having a valve member which is displaceable in the axial direction of the tubular hub in accordance with an embodiment.
Figure 4A:
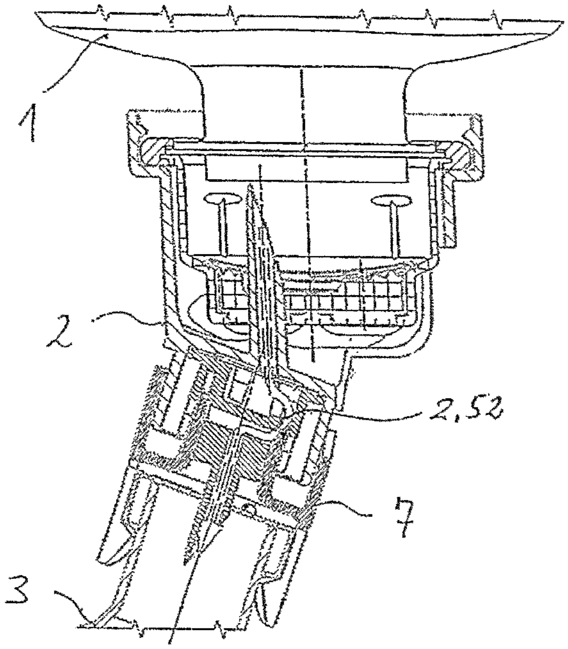

FIG. 4 shows a cross sectional view through the device having a valve member 7 which is displaceable in the axial direction of the tubular hub 2.3 in accordance with an embodiment. In this embodiment, a hub 2.51 is moulded on at the second hollow spike 2.5 and has a through-channel 2.52 (FIG. 4*a*) that can be sealed and unblocked by the displaceable valve member 7. FIG. 4 shows the closed position and FIG. 4*a* the open position, in which the sleeve-shaped valve member 7 is displaced toward the medicine container 3 so that the through-channel 2.52 is unblocked.

Figure 5:
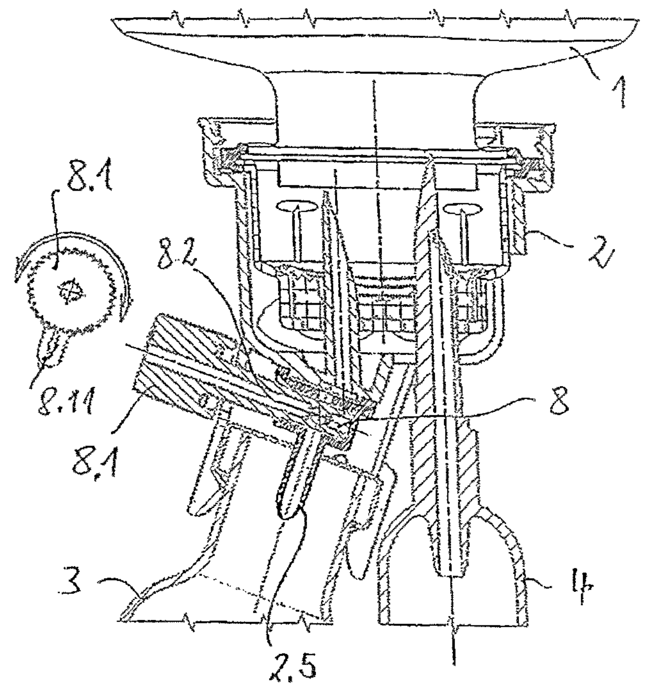
FIGS. 5 and 5*a* show a cross sectional view through the device having a valve with a twistable valve body and having an adjusting knob protruding from the transfer cap in accordance with an embodiment.
Figure 5A:
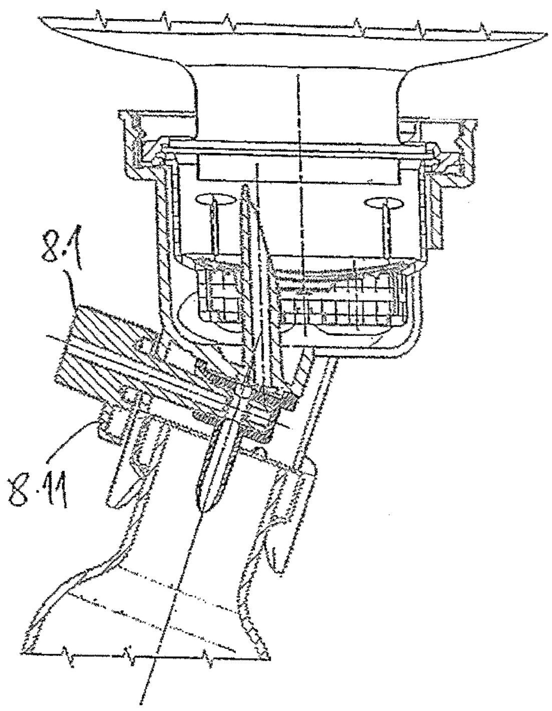

FIG. 5 shows a cross sectional view through the device having a valve with a twistable valve body and having an adjusting knob protruding from the transfer cap in accordance with an embodiment. In this embodiment, the valve is positioned between the first and second hollow spikes 2.4 and 2.5 arranged inclined to each other in the transfer cap 2, which has a twistable valve body 8 having an adjusting knob 8.1 protruding from the transfer cap 2. The shaft-shaped valve body 8 can be twisted in across-hole of a hub at the second hollow spike 2.5. The valve body 8 is provided with a through hole 8.2, which can be aligned with the second hollow spike 2.5 and a connecting opening to the first hollow spike 2.4 when the adjusting knob 8.1 is rotated into the open position denoted by a reference 8.11 as shown in FIG. 5*a*.

In the embodiments described, the medicine container 3 is set inclined to the vertical in the operating position at the transfer cap 2 so that the flow path between the first and second hollow spikes 2.4 and 2.5 is kept as minimal as possible. However, in an alternative embodiment, the transfer cap 2 may be made wider on the side of the medicine container 3, so that the medicine container 3 can likewise be positioned approximately vertically, that is, with its axis B approximately parallel to the axis A of the infusion container 1. Although this results in a longer flow path between the first and second hollow spikes 2.4 and 2.5 with the interposed valve, the flow path can be configured such that no disruptions occur during the mixing of the medicine.

In such an embodiment, a valve member can be provided between the first and second hollow spikes 2.4 and 2.5, which is displaceable transverse to the axes A and B of the infusion container 1 and of the medicine container 3, for opening and closing the connection between the two containers in the transfer cap 2.

Figure 6A:
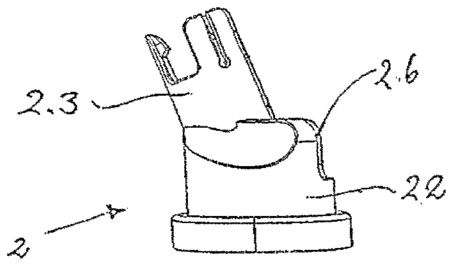
FIGS. 6*a*, 6*b* and 6*c* show perspective representations of the transfer cap in accordance with an embodiment.
Figure 6B:
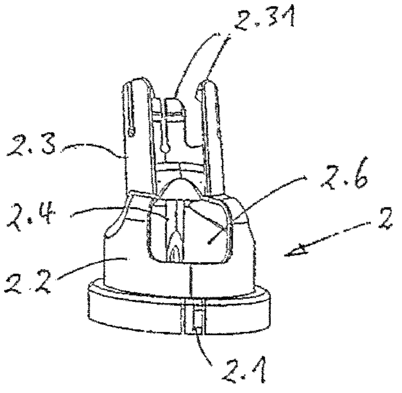
Figure 6C:
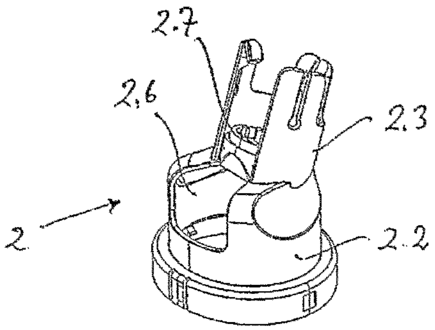

FIGS. 6*a*, 6*b* and 6*c* show perspective representations of the transfer cap 2 in accordance with an embodiment. In this embodiment, the second hollow spike 2.5 is formed as a separate component part, which is inserted at the partition wall 2.7 (FIG. 6*c*), not shown in FIGS. 6*b* and 6*c*.

Figure 8:
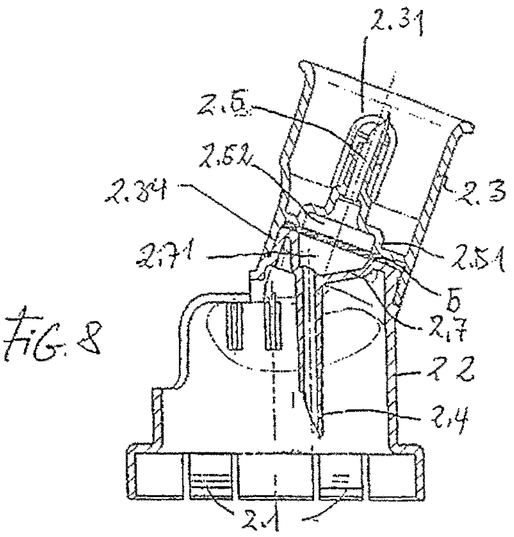
FIG. 8 shows a longitudinal section through a modified embodiment of the transfer cap.
Figure 9:
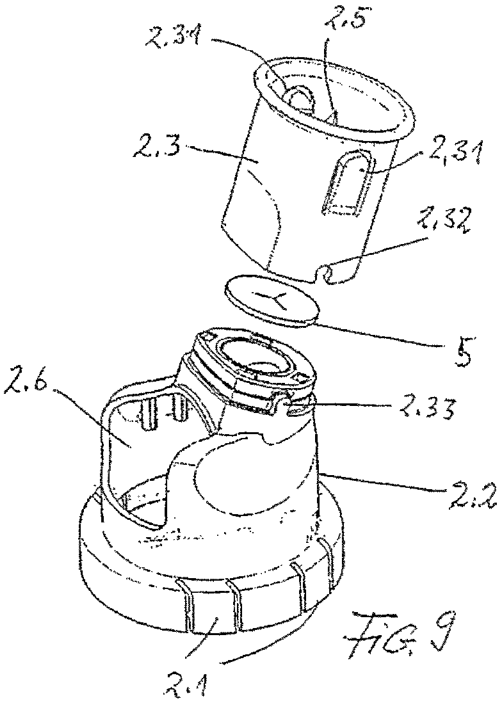
FIG. 9 shows a perspective view of the individual members of the embodiment according to FIG. 8.

In one embodiment, the transfer cap 2 may be formed in two parts such that the tubular hub 2.3 is attached to the hollow cylindrical portion 2.2 by means of detents, which simplifies the manufacture of the transfer cap 2. FIGS. 8 and 9 show a two-part embodiment of the transfer cap 2. As shown in FIG. 9, detent recesses 2.32 are formed at diametrically opposite positions at the lower edge of the tubular hub 2.3. The detent recesses 2.32 correspond to detent projections 2.33 formed at the upper circumference of the hollow cylindrical portions 2.2 when the tubular hub 2.3 is attached to the portion 2.2.

In this embodiment as shown in FIGS. 8 and 9, the first and second hollow spikes 2.4 and 2.5 are moulded onto the hollow cylindrical portion 2.2 and the tubular hub 2.3 of the transfer cap 2. The second hollow spike 2.5 is moulded on at a partition wall 2.51 in the tubular hub 2.3 such that a chamber 2.52 is created between the second hollow spike 2.5 and the valve 5. Detent recesses 2.32 shown in FIG. 9 are formed at the edge portion, denoted by 2.34 in FIG. 8, of the tubular hub 2.3.

As shown in FIG. 2, at the hollow cylindrical portion 2.2, the first hollow spike 2.4 is moulded on in a corresponding way at the partition wall 2.7, wherein the chamber 2.71 abutting at the valve disc 5 is formed larger in FIG. 8 than in FIG. 2.

The valve in the form of the valve disc 5 is clamped between the partition wall 2.7 of the hollow cylindrical portion 2.2 and the partition wall 2.51 of the tubular hub 2.3.

In the embodiment of FIGS. 8 and 9, the detents 2.31, as described in reference to FIG. 2, for receiving the medicine container 3, are formed as detent hooks formed at opposite positions on the circumference of the tubular hub 2.3 in this embodiment. At the hollow cylindrical portion 2.2, in place of the opposite detent portions 2.1, as described in reference to 6*b*, as shown in FIGS. 8 and 9 adjacent detent portions are formed such that altogether four detent portions 2.1 result.

In another embodiment, the first and second hollow spikes 2.4 and 2.5 are moulded on at the transfer cap 2 or at the partition wall 2.7 thereof, where the valve mechanism can be inserted laterally between the first and second hollow spikes, in a manner similar to the configuration shown in FIG. 5.

Figure 7:
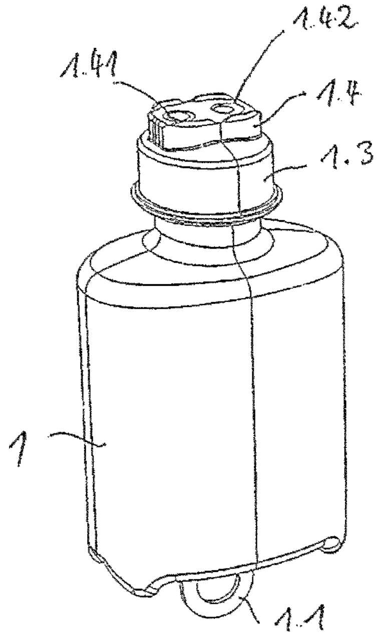
FIG. 7 shows a perspective view of the infusion container.

In one embodiment, the seal area 1.4 at the removal opening of the infusion container 1 can be configured such that there are two adjacent seal openings 1.41 and 1.42 in the cap 1.3, one of which is provided for the first hollow spike 2.4 of the transfer cap 2 and the other of which is provided for the hollow spike 4.1 of the drip chamber 4. FIG. 7 shows an approximately rectangular seal area 1.4 configured in such a manner at the infusion container 1, where the border of the rectangular seal area 1.4 is a part of the seal cap 1.3.

In this embodiment of the seal area 1.4, an aligning means can be moulded on at the transfer cap 2. Using the aligning means, the transfer cap 2 can be attached to the infusion container 1 or to the seal cap 1.3 only in such a manner that one of the openings 1.41 and 1.42 is located under the recess 2.6 and the other is located under the first hollow spike 2.4 of the transfer cap. In this way, incorrect positioning of the transfer cap 2 on the seal cap 1.3 is prevented.

In the embodiments described above, for example in FIG. 1, the medicine container 3 and the drip chamber 4 are arranged such that their axes lie essentially in one plane. In an alternative embodiment, the medicine container 3 and the tubular hub 2.3 are arranged inclined to the plane of the drawing in FIG. 1 so that in a right or a left side view in FIG. 2 the medicine container 3 lies inclined to the drip chamber 4 or inclined to the plane of the drawing in FIG. 2.

Although the present invention has been described with reference to specific embodiments, these embodiments are illustrative only and not limiting. Many other applications and embodiments will be apparent in light of this disclosure and the following claims.

What is claimed is:

1. A device for adding a medicine to an infusion solution in an infusion container comprising:

a transfer cap comprising a cylindrical portion having an exterior, an interior, and an opening sized and shaped to be connected to a nozzle of an infusion container having a seal with a first seal area and a second seal area;

a first hollow spike located in the interior of the cylindrical portion, said first hollow spike having a tip for piercing the first seal area of the nozzle when the transfer cap is connected to the infusion container and the opening surrounds the nozzle, said first hollow spike defining a first axis;

a cut out formed in the transfer cap defining a recess configured to allow an infusion spike access for piercing the second seal area of the infusion container in a side-to-side configuration with the first hollow spike so that the first hollow spike and the infusion spike directly connect to the infusion container;

a receiving hub having an opening for receiving a medicine container having a seal area located with the cylindrical portion, the receiving hub having a second hollow spike having a tip for piercing the seal area of the medicine container when the medicine container is received at the opening of the receiving hub, said second hollow spike defining a second axis;

a valve arranged between the first and second hollow spikes in the transfer cap; and wherein the valve is operable to interrupt fluid flow between the first hollow spike and the second hollow spike and wherein the second axis is disposed at an acute angle greater than zero in the clockwise direction to the first axis.

2. The device according to claim 1, wherein the receiving hub has an opening defining a plane and wherein the first axis is disposed at an angle to the plane of the opening of the receiving hub.

3. The device according to claim 1, wherein a medicine container is received in the receiving hub and wherein the medicine container is positioned inclined to a lengthwise axis of the transfer cap.

4. The device according to claim 1, wherein the receiving hub comprises detents for engaging a medicine container.

5. The device according to claim 1, wherein the valve is disposed entirely within the interior of the transfer cap.

6. The device according to claim 1, wherein the valve is formed as a resilient valve disc and positioned entirely between the first and second hollow spikes.

7. The device according to claim 1, wherein the valve comprises at least one slit which can be opened by fluid pressure.

8. The device according to claim 1, wherein the valve comprises a valve disc having a passage opening, wherein the valve disc is rotatable by a medicine container when the medicine container is connected to the receiving hub to align the passage opening with the first and second hollow spikes.

9. The device according to claim 1, wherein the opening of the transfer cap comprises a locking portion for mechanically engaging a nozzle of an infusion container.

10. The device according to claim 1, wherein the valve comprises a valve body having a passage opening, the valve body being displaceable along the second axis to open the passage opening for fluid flow.

11. The device according to claim 1, wherein an infusion container is attached to the opening of the transfer cap and the first spike punctures a seal of the infusion container, a medicine container is attached to the receiving hub, and a third spike comprising a tip extends through a recess area of the transfer cap.

12. The device according to claim 11, wherein a drip chamber extends from the third spike.

13. A device for adding a medicine to an infusion solution comprising:

a hollow cylindrical member having an opening sized and shaped to connect to a nozzle of an infusion container, the hollow cylindrical member defining an interior cavity comprising a first hollow spike for piercing a first seal area of the infusion container and a cut out defining a recess for access by an infusion spike to pierce a second seal area of the infusion container in a side-to-side configuration with the first hollow spike so that the first hollow spike and the infusion spike directly connect to the infusion container;

a tubular hub comprising a second spike coupled to the hollow cylindrical member, said tubular hub sized and shaped to receive a container and the first hollow spike and the second hollow spike pointing in different directions; and a valve positioned between the first and second hollow spikes, wherein the valve is manipulatable by force to open the valve and allow flow between the first hollow spike and the second hollow spike.

14. The device of claim 13, wherein the tubular hub defines a lengthwise axis and the hollow cylindrical member defines a lengthwise axis and wherein the two lengthwise axes are angled to one another.

15. The device of claim 13, wherein a tip of the first hollow spike is recessed within the interior cavity of the hollow cylindrical member.

16. The device of claim 13, wherein the valve comprises a rotatable valve disc which is provided with a passage opening, wherein a rotation of the valve disc about an axis of the second spike aligns the passage opening with the first and second hollow spikes positioned on opposite sides of the valve disc.

17. The device of claim 13, wherein the valve is displaceable about an axis of the second spike to open a flow passage.

18. A method for adding a medicine to an infusion solution in an infusion container having a nozzle provided with a seal area comprising:

coupling a hollow cylindrical member having an opening sized and shaped to connect to a nozzle of an infusion container and a first hollow spike and piercing the seal area on the nozzle with the first hollow spike, said hollow cylindrical member comprising a cut out defining a recess for access by an infusion spike to pierce a second seal area of the infusion container in a side-to-side configuration with the first hollow spike so that the first hollow spike and the infusion spike directly connect to the infusion container;

coupling a medicine container with a seal area to a tubular hub that has a second hollow spike located with the hollow cylindrical member so that the seal area of the medicine container is pierced by the second hollow spike; and actuating a valve positioned between the first and second hollow spikes to open the valve and allow flow through the first hollow spike and the second hollow spike from between the infusion container and the medicine container.

19. The method of claim 18, wherein actuating the valve comprises rotating the valve to align a passage opening through the valve with the first and second hollow spikes positioned on opposite sides of the valve.

20. The method of claim 19, wherein actuating the valve comprises displacing the valve in an axial direction of the tubular hub.

* * * * *

UNITED STATES PATENT AND TRADEMARK OFFICE

CERTIFICATE OF CORRECTION

PATENT NO. : 8,647,320 B2
APPLICATION NO. : 12/680734
DATED : February 11, 2014
INVENTOR(S) : Proksch et al.

It is certified that error appears in the above-identified patent and that said Letters Patent is hereby corrected as shown below:

On the Title Page

In column 1 Item (75) (Inventors), line 2, delete “Leeds” and insert --Muenchen--, therefor.

In the Specification

In column 3, line 22, delete “having,” and insert --having--, therefor.

In column 3, line 47, delete “piercable” and insert --pierceable--, therefor.

In column 7, line 32, delete “across-hold” and insert --a cross-hole--, therefor In column 7, line 33, delete “through hole” and insert --throughhole--, therefor.

In column 8, line 29, delete “6b,” and insert --FIG. 6b,--, therefor.

In column 8, line 60, delete “FIG. 1” and insert --FIG. 1,--, therefor.

Signed and Sealed this
Twelfth Day of August, 2014

Michelle K. Lee

Michelle K. Lee
*Deputy Director of the United States Patent and Trademark Office*